US008577051B2

(12) United States Patent
Miseki et al.

(10) Patent No.: US 8,577,051 B2
(45) Date of Patent: Nov. 5, 2013

(54) SOUND SIGNAL COMPENSATION APPARATUS AND METHOD THEREOF

(75) Inventors: Kimio Miseki, Tokyo (JP); Norikatsu Chiba, Tokyo (JP); Yasuhiro Kanishima, Tokyo (JP)

(73) Assignee: Kabushiki Kaisha Toshiba, Tokyo (JP)

(*) Notice: Subject to any disclaimer, the term of this patent is extended or adjusted under 35 U.S.C. 154(b) by 202 days.

(21) Appl. No.: 13/093,601

(22) Filed: Apr. 25, 2011

(65) Prior Publication Data

US 2011/0261971 A1 Oct. 27, 2011

(30) Foreign Application Priority Data

Apr. 26, 2010 (JP) ................................ 2010-101387

(51) Int. Cl.

*A61F 11/06* (2006.01)
*G10K 11/16* (2006.01)
*H03B 29/00* (2006.01)

(52) U.S. Cl.

USPC ........ 381/71.6; 381/71.8; 381/71.14; 381/74; 381/370; 381/56; 381/58

(58) Field of Classification Search

USPC .......... 381/71.6, 71.8, 71.14, 74, 370, 56, 58, 381/71.1, 71.2, 23.1, 317, 318, 320, 57, 381/94.1, 93

See application file for complete search history.

(56) References Cited

U.S. PATENT DOCUMENTS

2009/0208027 A1* 8/2009 Fukuda et al. ............... 381/71.6
2009/0296949 A1 12/2009 Iwata et al.

FOREIGN PATENT DOCUMENTS

| | | |
|---|---|---|
| JP | 04-018900 | 1/1992 |
| JP | 2008-182509 | 8/2008 |
| JP | 2009-194769 | 8/2009 |
| JP | 2009-288555 | 12/2009 |
| JP | 2010-081071 | 4/2010 |

OTHER PUBLICATIONS

Japanese Patent Application No. 2010-101387; Notice of Rejection; Mailed Sep. 6, 2011 (with English translation).

* cited by examiner

*Primary Examiner* — Vivian Chin
*Assistant Examiner* — Paul Kim
(74) *Attorney, Agent, or Firm* — Blakely, Sokoloff, Taylor & Zafman LLP

(57) ABSTRACT

According to one embodiment, a sound signal compensation apparatus includes an input module, a compensation module, and an output module. The input module receives identification information identifying a first frequency with regard to a resonance of an ear closed by an earphone or headphone. The compensation module performs first compensation emphasizing a second frequency on a sound signal, the second frequency being determined based on the identification information or the first frequency. The output module outputs the compensated sound signal. The compensation module is configured to perform the first compensation emphasizing the second frequency, at which emphasis is greater than or equal to 2 dB and less than or equal to 12 dB.

10 Claims, 15 Drawing Sheets

SOUND SIGNAL COMPENSATION APPARATUS AND METHOD THEREOF

CROSS-REFERENCE TO RELATED APPLICATIONS

This application is based upon and claims the benefit of priority from Japanese Patent Application No. 2010-101387, filed on Apr. 26, 2010, the entire contents of which are incorporated herein by reference.

FIELD

Embodiments described herein relate generally to a sound signal compensation apparatus and a method thereof.

BACKGROUND

Conventionally, there is known a resonance phenomenon induced in a space formed by an ear and an earphone/headphone when a user listens to music through the earphone/headphone. Such resonance phenomenon causes the user to hear unnatural sound. Thus, there has been proposed a system for cancelling the resonance phenomenon induced in the space formed by the ear and the earphone/headphone to fix the sound.

However, in the conventional technology, a user may still feel a sense of discomfort even when the resonance phenomenon in the space formed by the ear and the headphone is cancelled, because of the fact that the ear is closed by the headphone.

BRIEF DESCRIPTION OF THE SEVERAL VIEWS OF THE DRAWINGS

A general architecture that implements the various features of the invention will now be described with reference to the drawings. The drawings and the associated descriptions are provided to illustrate embodiments of the invention and not to limit the scope of the invention.

DETAILED DESCRIPTION

In general, according to one embodiment, a sound signal compensation apparatus comprises: an input module, a compensation module, and an output module. The input module is configured to receive identification information identifying a first frequency with regard to a resonance of an ear closed by an earphone or headphone. The compensation module is configured to perform first compensation emphasizing a second frequency on a sound signal, the second frequency being determined based on the identification information or the first frequency. The output module is configured to output the compensated sound signal. The compensation module is configured to perform the first compensation emphasizing the second frequency, at which emphasis is between greater than or equal to 2 dB and less than or equal to 12 dB.

In the following, an earphone, a headphone, and an ear are in singular form for simplicity of explanation. However, embodiments below are not limited thereto, and the sound signal compensation apparatus and the method thereof can be applied to a pair of earphones, both ears, and to both right and left sides of the headphone.

Figure 1:
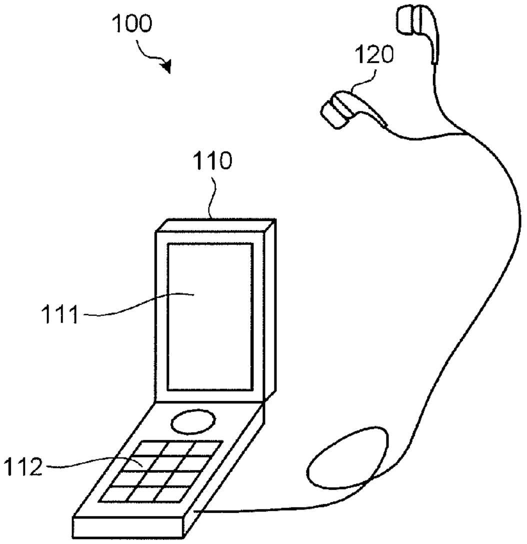
FIG. 1 is an exemplary schematic diagram of a sound processing apparatus according to a first embodiment.

FIG. 1 is an exemplary schematic diagram illustrating a sound processing apparatus 100 according to a first embodiment. As illustrated in FIG. 1, in the first embodiment, a sound signal compensation apparatus is applied to a sound processing apparatus such as a portable audio player. The sound processing apparatus 100 of FIG. 1 comprises a sound reproducer 110 and an earphone 120.

The sound reproducer 110 comprises clamshell housings connected to each other by a hinge not illustrated. A display 111 and an operation input module 112 are provided to an internal face of the clamshell housings, respectively. The earphone 120 is a canal type earphone or the like, and used when it is placed in an ear of a listener. In the first embodiment, the canal type earphone 120 is explained. However, other types of earphone or a headphone may be used.

When the sound signal compensation apparatus is applied to the sound processing apparatus, it is not limited that the sound signal compensation apparatus is installed in the sound reproducer. In other words, the sound signal compensation apparatus may be installed in an earphone or headphone, or may externally be connected to and in between the sound reproducer and an earphone.

Figure 2:
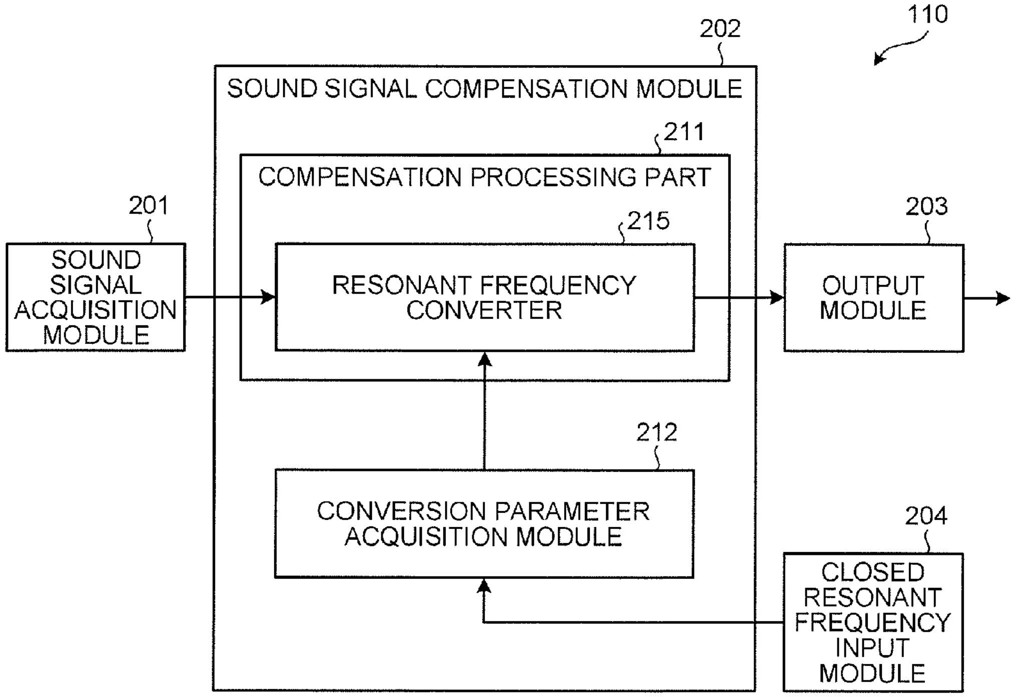
FIG. 2 is an exemplary functional block diagram of a sound reproducer of the first embodiment.

FIG. 2 is a functional block diagram of the sound reproducer 110 according to the first embodiment. As illustrated in FIG. 2, the sound reproducer 110 comprises a sound signal acquisition module 201, a sound signal compensation module 202, an output module 203, and a closed resonant frequency input module 204.

In the sound reproducer 110 of FIG. 2, a sound signal filtered by a filter coefficient acquired by a conversion parameter acquisition module 212 is output to the earphone 120 through the output module 203. In this case, the sound signal undergoes compensation at the sound signal compensation module 202 of the sound reproducer 110, and output as a sound signal from the sound reproducer 110. Here, the output module 203 is only necessary to be connected to the earphone 120.

The sound signal acquisition module 201 acquires a sound signal generated by a sound signal generator (not illustrated) of the sound reproducer 110 or a sound signal input from a memory or an external terminal not illustrated.

The sound signal acquired by the sound signal acquisition module 201 is a sound source to be used for reproduction, and is a target of sound signal compensation. The sound signal may be an audio signal of music or the like. On the other hand, the sound signal may be compressed data such as encoded audio data, encoded voice data, or lossless encoded data, or may be an audio wave signal acquired by performing appropriate decoding process. The sound reproducer 110 outputs the audio signal through 2 channels of left and right, but may output the audio signal in monaural or through multi channels. Thus, when the sound signal is reproduced, appropriate compensation is performed thereon in accordance with the number of channels.

The closed resonant frequency input module 204 inputs identification information identifying a resonant frequency (hereinafter, referred to as closed resonant frequency) induced in a space (hereinafter, referred also to as closed space or confined space) confined when the earphone or the headphone is placed in the ear. The identification information identifying the closed resonant frequency may be information about user's operation for identifying the closed resonant frequency, or may be information of a result of resonance-related measurement (for example, a first closed resonant frequency identified as being induced in the closed space) performed on user's ear. The closed resonant frequency input module 204 outputs the input information to the conversion parameter acquisition module 212.

The closed resonant frequency input module 204 may measure the closed resonant frequency of a user's ear to input the information. For example, the closed resonant frequency can be measured by outputting a sound signal to the confined space formed by the ear and the earphone/headphone, by collecting and analyzing the output signal through a microphone, and by obtaining a resonant peak at a certain frequency.

Further, the closed resonant frequency can be measured by other technique. In particular, a plurality of types of special signal processing for suppressing the closed resonance are performed on a test sound or music, and the test sound or music is output as a plurality of types of sound signal. Then, the reproduced sounds corresponding to the types of the sound signal are heard by a user through the earphone/headphone which is placed in the user's ear, and one of the types of the signal processing that is appropriate for hearing the sound signal is selected by the user (for example, via the operation input module 112) on a basis of sense of sound increase caused by the resonance. Here, each of the types of the signal processing is set to compensate different resonant frequency. Consequently, the closed resonant frequency input module 204 can selectively determine a closed resonant frequency which should be compensated for each user, in response to the user's selection.

The identification information identifying the closed resonant frequency may be any information capable of identifying the closed resonant frequency. For example, the identification information may be a value of the closed resonant frequency, or a type of the closed resonant frequency. When the number of candidates of the closed resonant frequencies are preliminarily listed as mentioned above in the case when one of the closed resonant frequency is selected, the identification information may be information (for example, index information) identifying certain candidate among the number of candidates. For example, when there are eight types of resonant frequencies or candidates, each of the types or the candidates can preliminarily be attached with numbers (indexing).

The sound signal compensation module 202 comprises the conversion parameter acquisition module 212 and a compensation processing part 211. The compensation processing part 211 comprises a resonant frequency converter 215. The sound signal compensation module 202 performs compensation processing on the sound signal.

Figure 3:
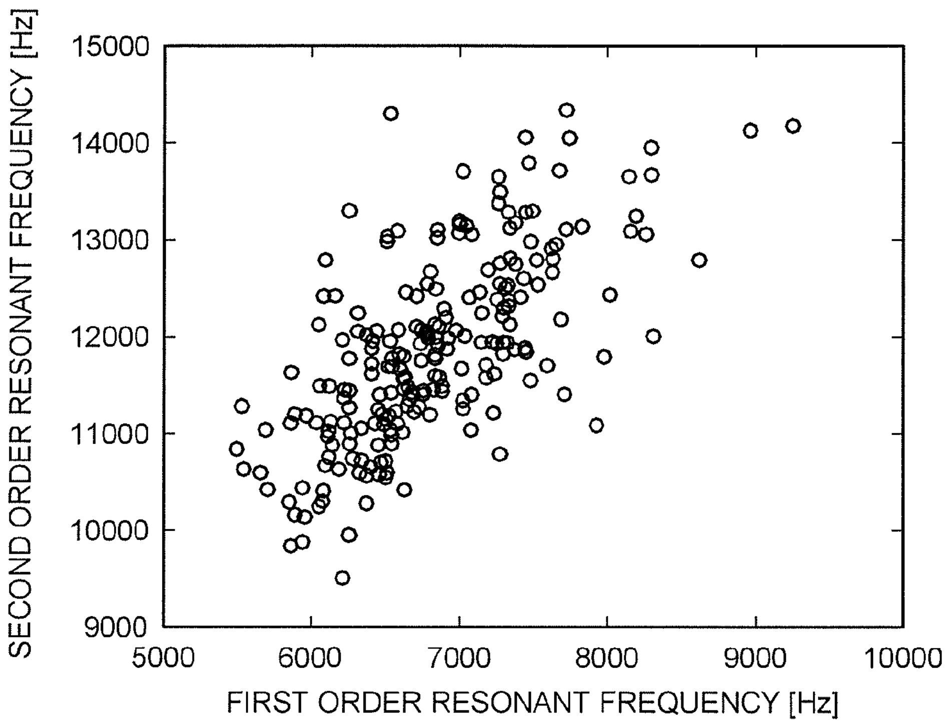
FIG. 3 is an exemplary graph illustrating distribution of first order resonant frequencies and second order resonant frequencies acquired from a number of subjects, in the first embodiment.

Conventionally, when music is heard by a user through an earphone/headphone, resonance phenomenon is induced in a space formed by the ear and the earphone/headphone. This is because the resonance phenomenon is caused in a space including an ear canal which is closed by the earphone/headphone. FIG. 3 is a graph illustrating distribution of first order resonant frequencies and second order resonant frequencies obtained from a number of subjects. As illustrated in FIG. 3, the resonant frequencies differ for each subject.

As described, when a user wears an earphone/headphone, the user hears unnatural sound in which signal component of the closed resonant frequency is amplified due to the resonance phenomenon induced within the closed space. The unnatural sound gives the user a feeling of hearing muffled sound or non-open sound. Thus, the sound reproducer 110 of the first embodiment suppresses the muffled sound from the unnatural sound induced in the space formed by the ear and the earphone/headphone, and compensates the sound to obtain open sound.

First, principals applied to various devices such as the one in the first embodiment or in later-described embodiments are explained. The sound reproducer 110 and a sound reproducer of other embodiments not only perform the compensation to suppress the closed resonant frequency, but also perform compensation for rendering open feeling (i.e., for obtaining the open sound) when the earphone/headphone is removed from the ear. Here, the closed resonant frequency to be suppressed by the compensation differs for different combinations of an earphone/headphone and a user who wears the earphone/headphone. The compensation for obtaining the open sound adaptively adds or emphasizes an open resonance which differs for each user, by establishing a relationship between the open resonance and the closed space formed by the ear of the user and the earphone/headphone. Here, the open resonance is assumed to be induced when each user hears sound from outside environment while the user is not wearing an earphone/headphone, or while the earphone/headphone is being removed from the ear. That is to say, when the open resonance is induced by the sound signal, the user recognizes the sound signal as that of the open sound.

The sound reproducer 110 of the first embodiment and the sound reproducer of the later-described embodiments convert the closed resonant frequency having a resonance property of the closed space formed by the ear and the earphone/headphone to a frequency having an open resonance property. Consequently, the frequency can be converted to a frequency which is felt by the user as natural, in accordance with physical phenomenon in real world natural environment. Next, a difference between an environment under which the closed resonance occurs in each closed space and an environment under which the open resonance occurs is explained.

Figure 4:
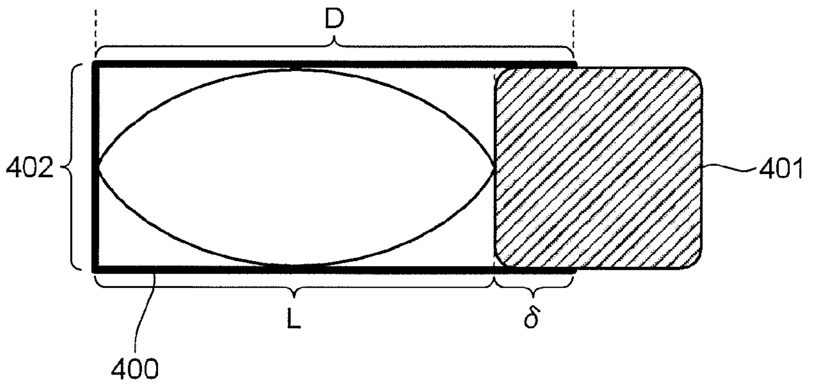
FIG. 4 is an exemplary schematic diagram of a model of a resonance induced in a closed space of an ear formed when an earphone is placed in the ear, in the first embodiment.

FIG. 4 is a schematic diagram of a resonance induced in the closed space formed when the earphone is placed in the ear. FIG. 4 illustrates an earphone 401 placed with respect to an acoustic tube 400, which models the ear canal. The acoustic tube 400 of FIG. 4 representing the ear canal has a length D. In FIG. 4, the earphone 401 is squeezed into the acoustic tube 400 representing the ear canal by a length δ, and placed with respect to the acoustic tube 400. A left end 402 of the acoustic tube 400 represents an eardrum side. FIG. 4 illustrates a case when the earphone 401 is placed in the ear. However, the embodiment is not limited thereto, and a headphone or the like may be placed in the ear instead of the earphone 401, as long as the closed space is formed.

In the example illustrated in FIG. 4, the closed space formed by the earphone 401 in place and the acoustic tube 400 representing the ear canal is represented by a closed tube of a length L. The length L is obtained by subtracting the length δ from the length D (L=D−δ). The length D differs for each individual, and the length δ changes in accordance with different combination of the user and the earphone worn by the user. When sound is reproduced in the closed space, the length L largely affects on the resonant frequency.

FIG. 4 illustrates a standing wave of a fundamental (i.e. first order) resonance in the closed tube of length L. The standing wave of the fundamental resonance has an antinode at the middle of the length L and nodes at the left end 402 of the acoustic tube and a left end of the earphone 401. Although not illustrated in FIG. 4, it is known that resonance of 2nd order or higher order (or overtone) resonances are also induced in the acoustic tube. Those overtone resonances may also be compensated.

A resonant frequency (hereinafter, referred to as closed resonant frequency) $F_{close}$ of the closed space of when the earphone/headphone is placed in the ear may be specified for each individual by various techniques described later. Once the closed resonant frequency $F_{close}$ is specified, the length L of the closed space formed by the earphone/headphone and the ear canal may be calculated by following equation (1).

$$L=(\lambda_{close})/2=(\upsilon/F_{close})/2 \tag{1}$$

Here, the variable υ represents sound velocity, and $\lambda_{close}$ represents wave length of the standing wave of the fundamental resonance in the closed tube of length L. From equation (1), following equation (2) can be obtained.

$$F_{close}=\upsilon(2L) \tag{2}$$

Figure 5:
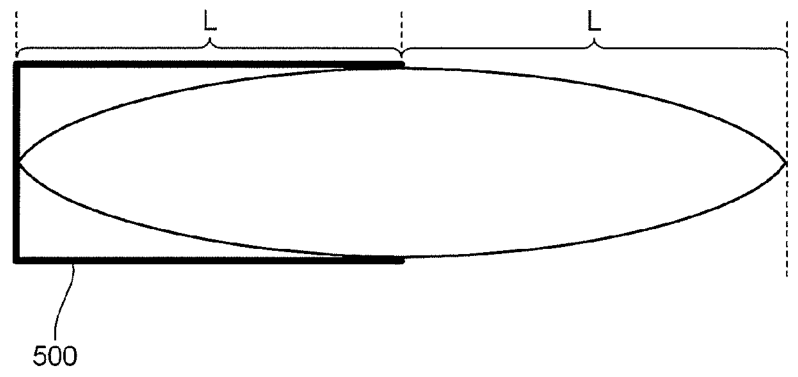
FIG. 5 is an exemplary schematic diagram of a first model of a resonance induced when the earphone is removed from the ear, in the first embodiment.

Next, a resonant frequency (hereinafter, referred to as open resonant frequency) $F_{open}$ of the open resonance of when the earphone/headphone is removed from the ear is considered. FIG. 5 is a diagram modeling the open resonance induced when the earphone 401 of FIG. 4 is removed. In FIG. 5, a right end of an acoustic tube 500 is opened because FIG. 5 models the ear canal with the earphone 401 being removed. Note that FIG. 5 does not take into account the length δ.

FIG. 4 illustrates the closed tube of length L. FIG. 5 illustrates the open resonance (fundamental open resonance) of when the right hand of the acoustic tube 500 of length L is opened. As illustrated in FIG. 5, in the acoustic tube 500, the fundamental open resonance has a node at a left end of the acoustic tube 500 and an antinode at a right end of the acoustic tube 500, which is opened. In this case, the open resonant frequency $F_{open}$ of the open resonance may be obtained by following equation (3).

$$F_{open}(L)=\upsilon/(4L)=(F_{close})/2 \tag{3}$$

By using equation (3), the closed resonant frequency $F_{close}$ of the resonance induced in the closed space formed when the earphone is in place can be converted into the open resonant frequency $F_{open}$ (L) of the open resonance. In FIG. 5, it can be understood from equation (3) that the open resonant frequency $F_{open}$ (L) of the open resonance is obtained by multiplying the closed resonant frequency $F_{close}$ by γ (γ=0.5). Here, FIG. 5 is only a schematic of the acoustic tube 500, thereby γ could be any value near 0.5. For example, γ may approximately be within the range from 0.4 to 0.6.

Figure 6:
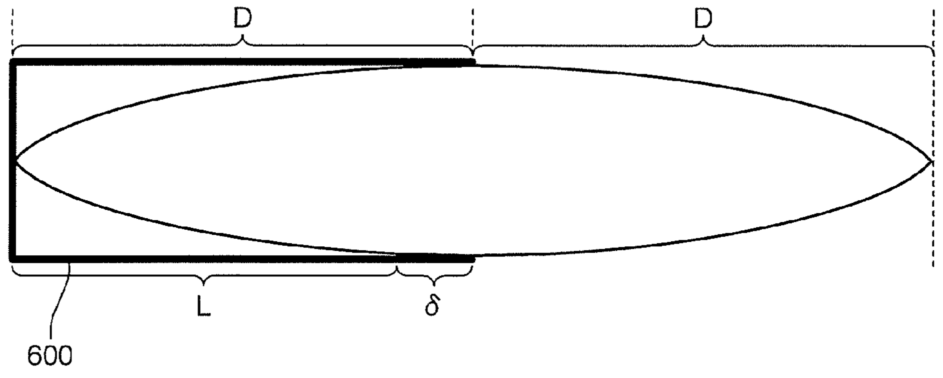
FIG. 6 is an exemplary schematic diagram of a second model of the resonance induced when the earphone is removed from the ear, in the first embodiment.

The calculation of the open resonant frequency $F_{open}$ is not limited to the technique illustrated in FIG. 5, but other techniques can be used. Next, an example taking into account the length δ, which corresponds to an amount of the earphone 401 squeezed into the ear canal, is explained. FIG. 6 illustrates an open resonance (fundamental open resonance) of when an acoustic tube 600 with its right end being opened is modeled by an ear canal of actual length D taking into account the length L of the closed space and the depth δ of when the earphone 401 is placed in the ear. As illustrated in FIG. 6, in the acoustic tube 600 with one side being opened, the fundamental open resonance has a node at a left end of the acoustic tube 600 and an antinode at a right end of the acoustic tube

600 which is opened. In this case, an open resonant frequency $F_{open}$ can be obtained by following equation (4).

$$F_{open}(D)=v/(4D)=v/(4(L+\delta) \quad (4)$$

That is to say, in FIG. 6, the open resonant frequency $F_{open}$ (D) is calculated from the closed resonant frequency $F_{close}$, while taking into account the depth δ of the earphone placement. The open resonant frequency $F_{open}$ (D) derived by equation (4) can be expressed by following inequality (5).

$$F_{open}(D)=\upsilon/(4(L+\delta))<(F_{close})/2 \quad (5)$$

In inequality (5), the open resonant frequency $F_{open}$ (D) is smaller than one-half of the closed resonant frequency $F_{close}$. That is to say, the open resonant frequency $F_{open}$ (D) is obtained by multiplying the closed resonant frequency $F_{close}$ by γ (γ<0.5).

When the sound signal is compensated by using the open resonant frequency $F_{open}$ (D) better environment can be provided for the user because the open resonant frequency is calculated by taking into account the fact that the earphone is actually squeezed into the ear canal.

That is to say, not only that the resonance due to the physical length L of the acoustic tube is suppressed, but the depth δ that is the amount of the earphone squeezed into the ear is also taken into account. Consequently, the open resonant frequency $F_{open}$(D) suitable for the relationship between when the earphone is placed in the ear and when the earphone is removed from the ear can be derived by applying the acoustic tube model of length D (>L) with its one side being opened. That is to say, not only that the confined sound or the muffled sound is suppressed, but natural open sound can be provided. Here, the depth δ can be calculated by any technique. For example, the user can select any δ from a number of selections, or a depth δ from actual measurement may be used.

Figure 7:
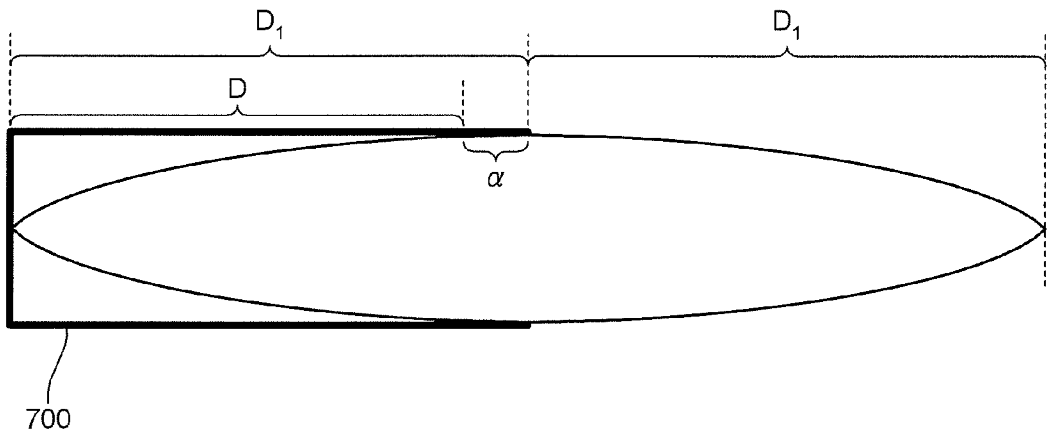
FIG. 7 is an exemplary schematic diagram of a third model of the resonance induced when the earphone is removed from the ear, in the first embodiment.

The present embodiment may take into account the auricle (pinna), which is located further out from the ear canal. FIG. 7 illustrates an open resonance (fundamental open resonance) modeled by an acoustic tube 700 with its right end being opened and having a length $D_1$, which takes into account the length L of the closed space, the depth δ that is the amount of the earphone 401 squeezed into the ear, and a thickness α of the auricle (or depth of the auricle). In FIG. 7, the acoustic tube 700 is modeled as a closed tube of the length $D_1$ which is longer than the length D, by including the thickness a of the auricle.

As illustrated in FIG. 7, there is an antinode of the fundamental open resonant frequency at the right end of the acoustic tube 700 of the length D1 including the thickness α of the auricle. In this case, the open resonant frequency $F_{open}$ can be expressed by following equation (6).

$$F_{open}(D_1)=v/(4D_1)=v/(4(L+\delta+\alpha)) \quad (6)$$

In equation (6), the thickness a of the auricle is, α>0. The closed resonant frequency $F_{close}$ induced in the closed space formed when the earphone is placed in the ear is converted to the open resonant frequency $F_{open}$(D1), based on the acoustic tube 700 of the length D1 (>D>L) with its one side being opened. Here, as mentioned before, the length D1 is a value taking into account the depth δ, which is the amount of the earphone squeezed into the ear, and the thickness α of the auricle. Then, this open resonant frequency $F_{open}$ (D1) is provided to the reproduction sound. Accordingly, compensation suitable for the real world situation taking into account the relationship between when the earphone is placed in the ear and when the earphone is removed from the ear. As a result, not only that the confined sound or the muffled sound of the reproduction sound is suppressed, but the natural open sound can be provided as the reproduction sound. The concept illustrated in FIGS. 5 to 7 can be applied not only to the present embodiment, but to embodiments or various modifications described later, or to various devices for listening to the reproduction sound. The same effect can be obtained by those applications.

In the following, FIGS. 5 to 7 are explained using a concrete example. For example, assume that the sound velocity υ=340 m/s, L=2.5 cm, D=3.5 cm, and $D_1$=4 cm. In this case, from equations (2) to (4) and (6), $F_{close}$=6800 HZ, $F_{open}$(L) =3400 Hz, $F_{open}$ (D)=2428.57 HZ, and $F_{open}$ ($D_1$)=2125 Hz can be calculated. The $F_{open}$ are calculated by multiplying the frequency $F_{close}$ by γ, where γ is within the range approximately from 0.3 to 0.5. This range is from approximate calculation based on the acoustic tube model, so in practice, γ may be within a range approximately from 0.2 to 0.6. Such range is not required to be precise, and the open sound can be obtained as long as a frequency (hereinafter, referred also to as open resonant frequency) close to the open resonant frequency (that differs for each user) is appropriately emphasized. In view of those frequencies, the following inequality (7) can be obtained.

$$F_{open}(D_1)<F_{open}(D)<F_{open}(L)=(F_{close})2<F_{close} \quad (7)$$

For the audio reproducer of the present embodiment, the embodiments described later, and the modifications described later, inequality (7) requires the open resonant frequency $F_{open}$ to be lower than the closed resonant frequency $F_{close}$. Here, the open resonant frequency $F_{open}$ is a frequency which is obtained by converting the closed resonant frequency $F_{close}$ and which is to be provided for the reproduction sound. More in details, the open resonant frequency $F_{open}$ is preferred to be obtained by multiplying the closed resonant frequency $F_{close}$ by γ (γ is a value between 0.2 and 0.6), as described above.

The open resonance of FIGS. 5 to 7 is obtained from the closed resonant frequency $F_{close}$ induced in the closed space formed when the earphone/headphone is placed in the ear. In the sound reproducer according to the present embodiment, the embodiments described later, and the modifications described later, processing is performed based on such relationship between the open resonant frequency $F_{open}$ and the closed resonant frequency $F_{close}$. Accordingly, it becomes capable of converting a frequency to the open resonant frequency, which is more natural and appropriate for real world physical phenomenon.

The conversion parameter acquisition module 212 acquires a conversion parameter used to convert the closed resonant frequency to an open resonant frequency of ear free from an earphone/headphone, based on the identification information identifying the closed resonant frequency from the closed resonant frequency input module 204. The open resonant frequency acquired by the conversion parameter acquisition module 212 is derived by the technique explained above with FIGS. 5 to 7. For example, the open resonant frequency is calculated by multiplying the closed resonant frequency by γ (γ is a value approximately within a range from 0.2 to 0.6). The actual value of γ is set appropriately in accordance with actual use condition, such as whether to take into account the shape of the earphone or the thickness of the auricle.

As described above, the conversion parameter acquisition module 212 determines the open resonant frequency of ear free from an earphone/headphone, which is lower than the closed resonant frequency, from the identification information. Then, the conversion parameter acquisition module 212 acquires a conversion parameter that converts the closed resonant frequency to the determined frequency. In other words, the conversion parameter acquisition module 212 obtains a conversion parameter that emphasizes a component of the open resonant frequency based on the identified closed resonant frequency. Here, the frequency of the emphasized component is lower than the identified closed resonant frequency. The conversion parameter acquired by the conversion parameter acquisition module 212 is output to the compensation processing part 211.

The effect of the compensation can be obtained only by emphasizing the component of the open resonant frequency by the conversion parameter obtained at the conversion parameter acquisition module 212. However, the conversion parameter is further configured to contain compensation suppressing the closed resonant frequency of the closed space. Consequently, the confined sound can be alleviated and high quality open sound can be provided to the user.

The compensation processing part 211 comprises the resonant frequency converter 215, and performs compensation processing on the sound signal input from the sound signal acquisition module 201.

During the compensation control by the compensation processing part 211, the resonant frequency converter 215 performs frequency conversion so that a resonant peak of the sound signal changes from the closed resonant frequency $F_{close}$ to the open resonant frequency $F_{open}$, by using the conversion parameter.

The resonant frequency converter 215 performs the frequency conversion on the sound signal that is input from the sound signal acquisition module 201, by using the conversion parameter input from the conversion parameter acquisition module 212, to suppress an amplitude of the closed resonant frequency $F_{close}$ and to emphasize the open resonant frequency $F_{open}$. Consequently, the resonance of when the earphone is placed in the ear and which is induced due to the physical length L of the acoustic tube is suppressed, and the open resonant frequency $F_{open}(L)$ is emphasized. Thus, when one side of the acoustic tube with the same aforementioned length L is opened, a user can hear natural sound which is similar to what the user would hear in the real world. Therefore, not only that the confined sound or the muffled sound can be suppressed, but the natural open sound can also be provided as the reproduction sound.

Figure 8:
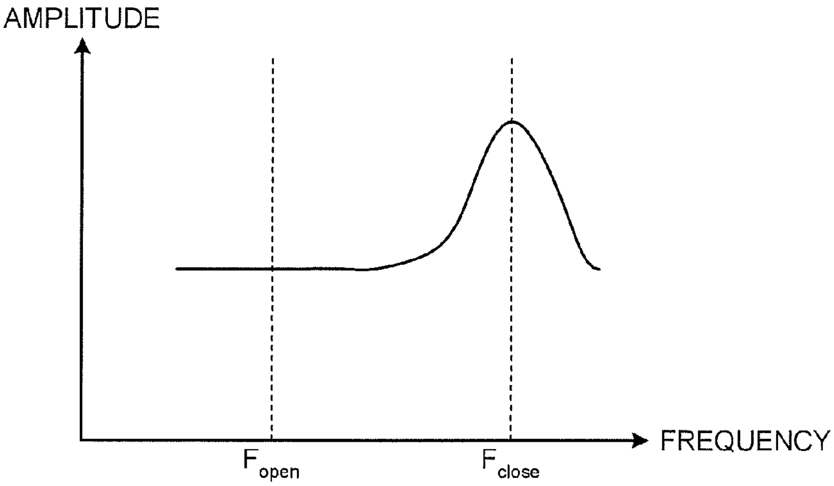
FIG. 8 is a first exemplary graph of a property of a resonance phenomenon occurred when an earphone/a headphone is placed in an ear and a sound source signal is output, in the first embodiment.

Next, a compensation property used in the compensation processing part 211 is explained. FIG. 8 is a graph illustrating a property of a resonance phenomenon induced when an earphone/headphone is placed in an ear and a sound source signal is output. FIG. 8 illustrates the closed resonant frequency $F_{close}$ specified as the resonant peak, and the open resonant frequency $F_{open}$. The open resonant frequency $F_{open}$ of FIG. 8 is determined from the closed resonant frequency $F_{close}$ by the conversion parameter acquisition module 212. That is to say, the open resonant frequency $F_{open}$ is obtained by multiplying the closed resonant frequency $F_{close}$ by $\gamma$ ($\gamma$ is a value approximately within a range from 0.2 to 0.6). That is, the user can hear the natural open sound when the resonant peak is at a frequency near the open resonant frequency.

Figure 9:
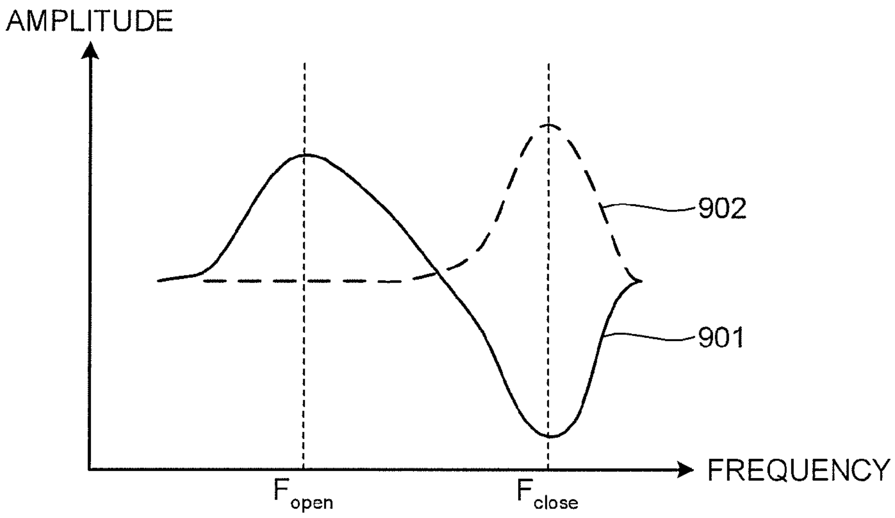
FIG. 9 is an exemplary graph of a compensation property to be applied to the resonance phenomenon of FIG. 8 by a compensation processing part in the first embodiment.

The compensation processing part 211 performs compensation by using filter coefficient information by the conversion parameter so that the resonant peak is obtained at the frequency near the open resonant frequency $F_{open}$. FIG. 9 illustrates a compensation property 901. The dashed line 902 illustrates the property of the resonance phenomenon shown in FIG. 8. A compensation property 901 of FIG. 9 is one example of a compensation property for suppressing the frequency component (amplitude) of the closed resonant frequency $F_{close}$ and for emphasizing the frequency component (amplitude) of the open resonant frequency $F_{open}$, which is lower than the closed resonant frequency $F_{close}$. The amplitudes of the closed resonant frequency $F_{close}$ and the open resonant frequency $F_{open}$ of the compensation property 901 can be set to appropriate values when actually applied. This is because, the confined sound can be reduced and the open sound can be obtained by only slightly suppressing the resonant peak of the closed resonant frequency $F_{close}$ and by only slightly emphasizing the frequency component of the open resonant frequency $F_{open}$. For example, the compensation processing part 211 may compensate the open resonant frequency $F_{open}$ by emphasizing the open resonant frequency by an amount within a range between greater than or equal to 2 or 3 dB and less than or equal to 12 dB.

Figure 10:
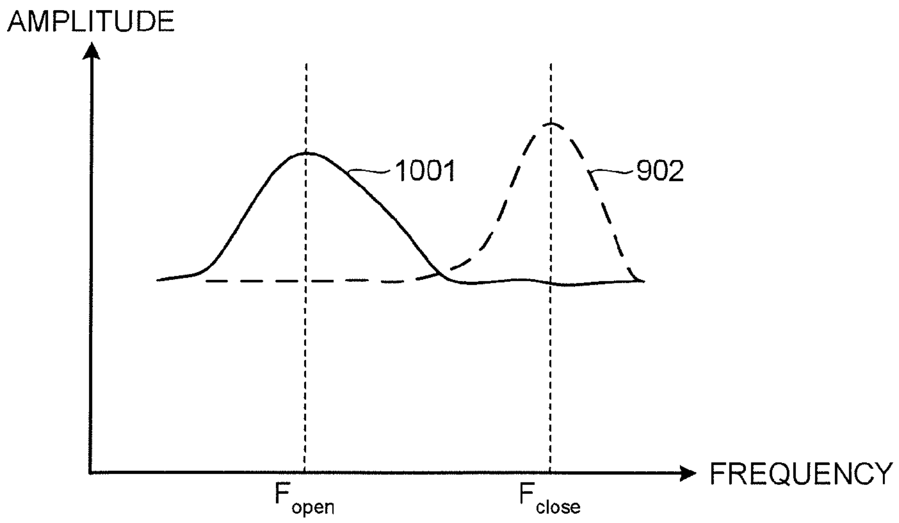
FIG. 10 is a graph of a property of compensated resonance by the compensation property of FIG. 9 by the compensation processing part in the first embodiment.

FIG. 10 is a graph illustrating a property 1001 of compensated resonance by the compensation property of FIG. 9. As illustrated in FIG. 10, the compensation processing part 211 performs the compensation on a sound source signal 902 so that the resonant peak is converted from the closed resonant frequency $F_{close}$ to the open resonant frequency $F_{open}$. That is to say, the compensation processing part 211 compensates the sound signal by a filter C(z) having the frequency property illustrated by the solid line in FIG. 9. Thus, it becomes possible realize the conversion process converting the closed resonant frequency $F_{close}$ to the open resonant frequency $F_{open}$.

Figure 11:
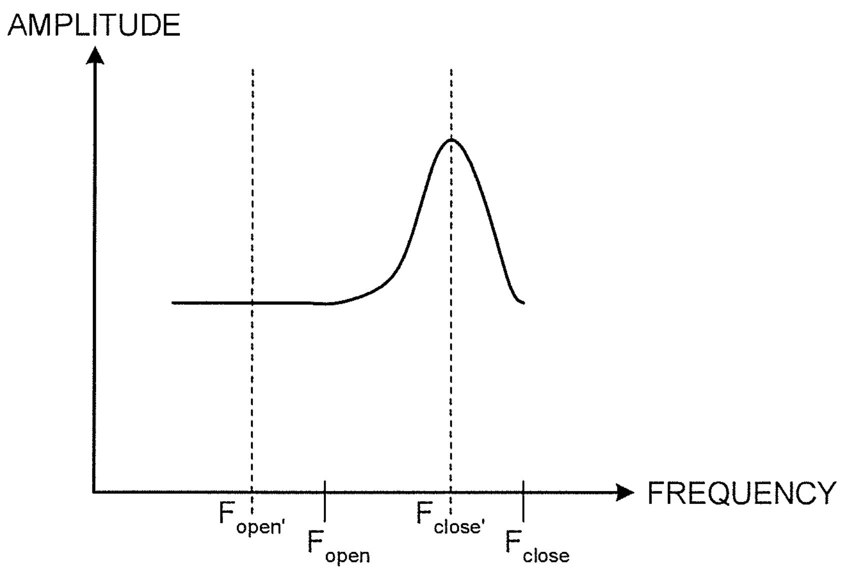
FIG. 11 is a second exemplary graph of a property of the resonance phenomenon induced when an earphone/a headphone is placed in an ear and a sound source signal is output, in the first embodiment.

FIG. 11 is a graph illustrating another example of the property of the resonance phenomenon induced when the earphone/headphone is placed in the ear and the sound source signal is output. FIG. 11 illustrates a closed resonant frequency $F_{close'}$ that is lower than the closed resonant frequency $F_{close}$ of FIG. 8. As is clear from the differences between FIGS. 8 and 11 and as mentioned before, the closed resonant frequency differs for each ear property and for each combination of individual and earphone/headphone. As illustrated in FIG. 11, when the closed resonant frequency (for example, $F_{close'}$) is low, the conversion parameter acquisition module 212 determines the open resonant frequency to a low value (for example, $F_{open'}$) based on the closed resonant frequency.

Figure 12:
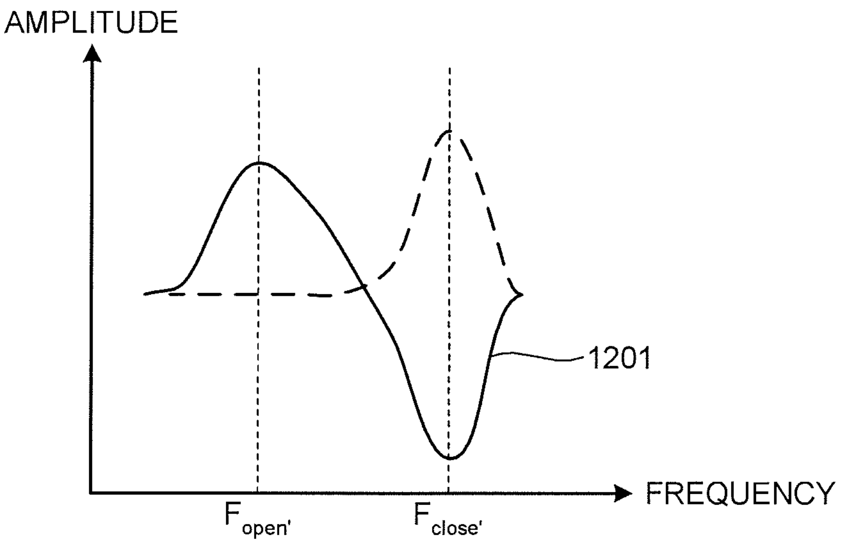
FIG. 12 is an exemplary graph of a compensation property to be applied to the resonance phenomenon of FIG. 11 by the compensation processing part in the first embodiment.

Then, the compensation processing part 211 performs compensation processing by using a compensation property 1201 of FIG. 12 as the compensation on the closed resonant frequency $F_{close'}$ illustrated in FIG. 11. As a result, a sound source signal after the compensation obtains a resonant property as illustrated in FIG. 13.

Figure 13:
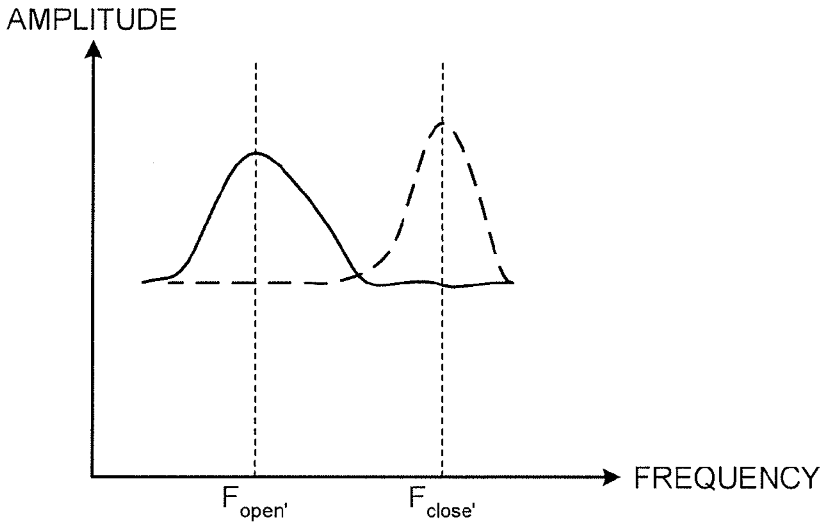
FIG. 13 is a graph of a property of compensated resonance by the compensation property of FIG. 12 by the compensation processing part in the first embodiment.

When the closed resonant frequency is high to the contrary of FIGS. 11 to 13, the conversion parameter acquisition module 212 determines the open resonant frequency to a higher value depending on the closed resonant frequency. As a result, the physical relation between the closed resonance and the open resonance of the ear in the real world can be automatically reflected by using a filter coefficient determined in the conversion parameter acquisition module 212 as a difference of resonance between when the earphone/headphone is worn and when not worn.

When the closed resonant frequency $F_{close}$ and the open resonant frequency $F_{open}$ are both fundamental resonance, the resonant frequencies are required to satisfy the relation; (open resonant frequency $F_{open}$)<(closed resonant frequency $F_{close}$).

Compensation processing performed by the compensation processing part 211 can be expressed by following equation (8).

$$y(n) = \sum_{i=0}^{M-1} c(i)x(n-i) \tag{8}$$

In equation (8), the filter coefficient c(i) (i=0, 1, . . . , M−1; where M is an order of the filter) is applied to the input sound signal x(n) to obtain the output sound signal y(n). Here, the filter coefficient c(i) (i=0, . . . , M−1) represents one example of the conversion parameter.

Referring back to FIG. 2, after the sound property of the sound signal is compensated by the sound signal compensation module 202, the output module 203 reproduces the compensated sound signal, and outputs it to the user's ear through the earphone 120.

In the sound reproducer 110, the sound signal obtained by the sound signal acquisition module 201 may be input to the sound signal compensation module 202 after other sound processing such as low-band emphasis, various sound effects, and/or the like, is performed on the sound signal obtained by the sound signal acquisition module 201. Further, the sound signal compensated by the sound signal compensation module 202 may be output to the output module 203 after other sound processing such as low-band emphasis, various sound effects, and/or the like, is performed on the sound signal compensated by the sound signal compensation module 202. Even if such a configuration as mentioned above is used, it is clear that the compensation effect of a sound signal is obtained. Thus, a sound reproducer comprising the aforementioned configuration is also comprised in the present embodiment and the later-described embodiments.

Figure 14:
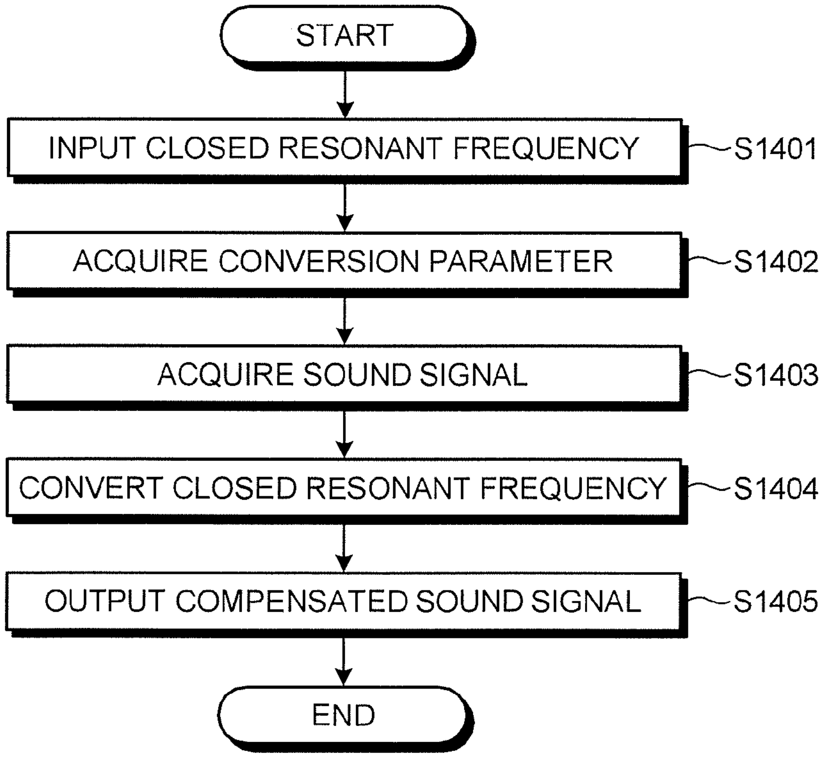
FIG. 14 is an exemplary flowchart of processes of the sound reproducer with respect to the sound signal in the first embodiment.

Next, processes of the sound reproducer 110 of the present embodiment with respect to the sound signal are explained. FIG. 14 is a flowchart of the aforementioned processes in the sound reproducer 110 of the present embodiment.

First, the closed resonant frequency input module 204 inputs the identification information identifying the closed resonant frequency (for example, closed fundamental resonant frequency) of when the earphone/headphone is placed in the ear (S1401). The closed resonant frequency input module 204 identifies the closed resonant frequency (for example, closed fundamental resonant frequency) induced when the earphone/headphone is placed in the ear, based on the user's operation or the result of measurement of the closed resonant frequency. Then, the closed resonant frequency input module 204 sends the identification information representing the identified closed resonant frequency to the sound signal compensation module 202.

Next, the conversion parameter acquisition module 212 acquires the conversion parameter (S1402). Here, the conversion parameter converts the closed resonant frequency to the frequency near the open resonant frequency of when the earphone/headphone is removed from the ear, based on the identification information identifying the closed resonant frequency. The conversion parameter may be beforehand stored in the conversion parameter acquisition module 212, or may be calculated based on the inputted closed resonant frequency.

Then, the sound signal acquisition module 201 acquires a sound signal, which is a sound source used for sound reproduction (S1403).

Then, the resonant frequency converter 215 in the compensation processing part 211 performs the resonant frequency conversion on the sound signal inputted from the sound signal acquisition module 201 by using the acquired conversion parameter (S1404). Consequently, the compensation processing to suppress the frequency component of the closed resonant frequency and emphasize the frequency component of the open resonant frequency is performed.

Subsequently, the output module 203 outputs a sound signal which experienced the compensation processing (S1405). As a result of the aforementioned processes by the sound reproducer 110, a user can hear reproduction sound without a feeling of the confined sound.

In the first embodiment, the compensation is performed based on the fundamental resonant frequency. However, the compensation is not limited thereto, and the compensation can be performed by using higher order (or overtone) resonant frequencies.

As described above, the sound reproducer 110 performs the compensation so that high quality sound can be provided to the user without providing the unnatural sound (such as confined sound or muffled sound) peculiar to an earphone/closed headphone. That is to say, according to the present embodiment, it becomes capable of eliminating the confined sound due to the closed resonance which is different for each individual. Accordingly, the user can enjoy the high quality and natural open sound.

In the first embodiment, the resonant frequency is converted by the resonant frequency converter 215 for the compensation. However, the compensation is not limited thereto, and the configuration for the compensation may be divided into two configurations. Namely, the compensation can be divided so as to be performed by a first configuration for suppressing the closed resonant frequency and a second configuration for emphasizing the open resonant frequency.

Figure 15:
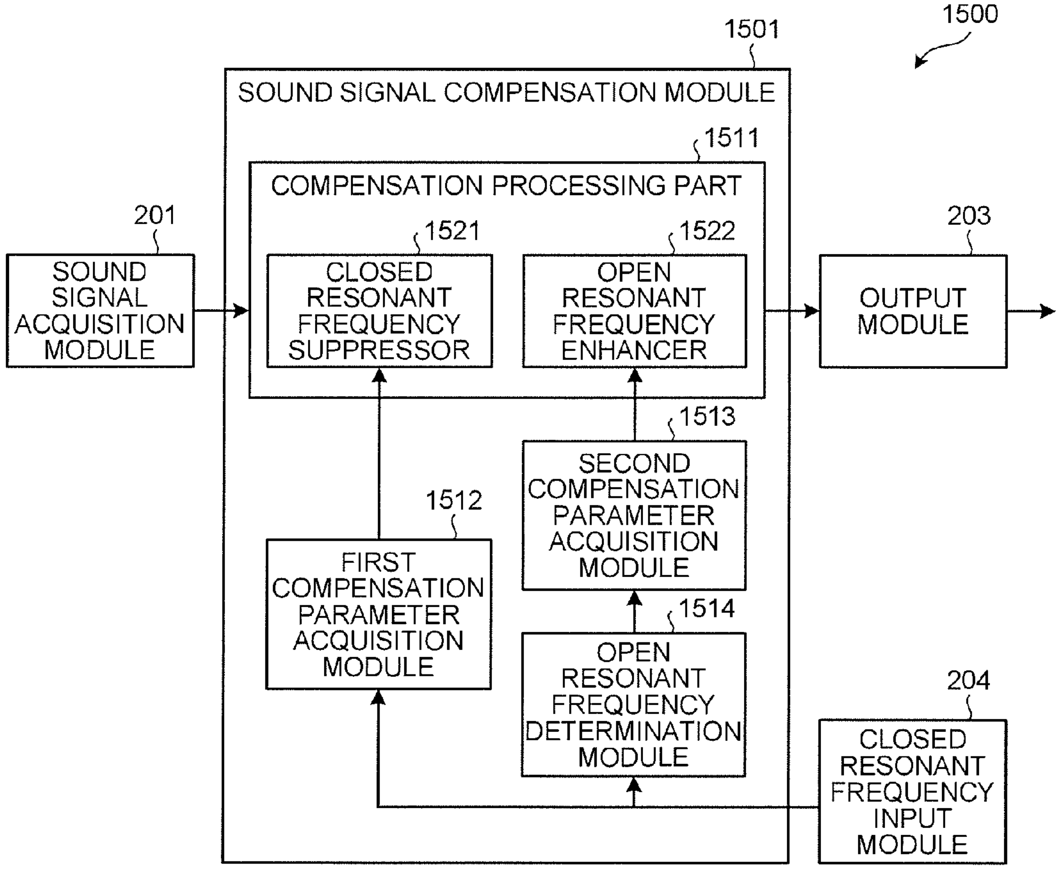
FIG. 15 is an exemplary block diagram of a sound reproducer according to a second embodiment.

FIG. 15 is a exemplary block diagram of a sound reproducer 1500 of a second embodiment. As illustrated in FIG. 15, the sound reproducer 1500 comprises the sound signal acquisition module 201, a sound signal compensation module 1501, the output module 203, and the closed resonant frequency input module 204. In the following explanation, elements identical to that of the aforementioned first embodiment are labeled with the same reference letters and numerals, and the explanation thereof are omitted.

In the sound signal compensation module 1501 of the second embodiment, the configuration for suppressing the closed resonant frequency and the configuration for emphasizing the open resonant frequency are separated from each other. Hence, a configuration of the sound signal compensation module 1501 differs from that of the sound signal compensation module 202.

The sound signal compensation module 1501 comprises a compensation processing part 1511, a first compensation parameter acquisition module 1512, a second compensation parameter acquisition module 1513, and an open resonant frequency determination module 1514.

The first compensation parameter acquisition module 1512 acquires, from identification information input from the closed resonant frequency input module 204, a parameter which suppresses a frequency component of the closed resonant frequency identified by the identification information. The acquired parameter is output to a closed resonant frequency suppressor 1521.

The open resonant frequency determination module 1514 determines an open resonant frequency from the identification information input from the closed resonant frequency input module 204 based on the closed resonant frequency. The technique to determine the open resonant frequency is the same as that of the first embodiment, thereby explanations thereof are omitted.

The second compensation parameter acquisition module 1513 acquires a parameter emphasizing a frequency component of the determined open resonant frequency. Then, the acquired parameter is output to an open resonant frequency enhancer 1522.

The compensation processing part 1511 comprises the closed resonant frequency suppressor 1521 and the open resonant frequency enhancer 1522, and performs compensation processing on an input sound signal.

The closed resonant frequency suppressor 1521 performs compensation on the sound signal by using the parameter input from the first compensation parameter acquisition module 1512, to suppress the frequency component of the closed resonant frequency.

The open resonant frequency enhancer 1522 performs compensation with respect to the sound signal by using the parameter input from the second compensation parameter acquisition module 1513, to emphasizes the frequency component of the open resonant frequency.

Figure 16:
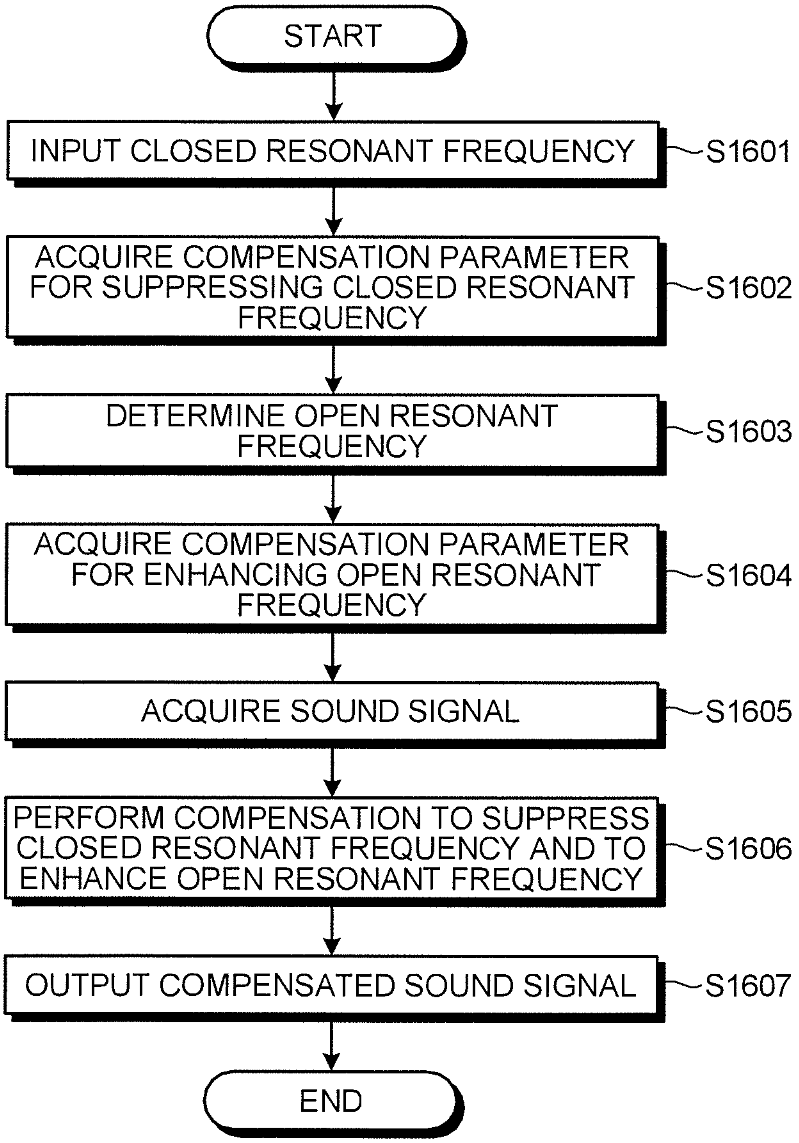
FIG. 16 is an exemplary flowchart of processes of the sound reproducer with respect to the sound signal in the second embodiment.

Next, processes of the sound reproducer 1500 of the present embodiment on the sound signal are explained. FIG. 16 is a flowchart illustrating the aforementioned processes of the sound reproducer 110 of the present embodiment.

First, the closed resonant frequency input module 204 inputs the identification information identifying the closed resonant frequency (for example, closed fundamental resonant frequency) of when the earphone/headphone is placed in the ear (S1601).

Next, the first compensation parameter acquisition module 1512 acquires, from the identification information identifying the closed resonant frequency, a compensation parameter for suppressing a frequency component of the closed resonant frequency (S1602).

The open resonant frequency determination module 1514 determines, from the identification information identifying input from the closed resonant frequency input module 204, the open resonant frequency which is based upon the closed resonant frequency (S1603).

Then, the second compensation parameter acquisition module 1513 acquires a compensation parameter for emphasizing a frequency component of the determined open resonant frequency (S1604).

The sound signal acquisition module 201 then acquires a sound signal, which is a sound source to be used for sound reproduction (S1605).

Then, the closed resonant frequency suppressor 1521 performs first compensation and the open resonant frequency enhancer 1522 performs second compensation (S1606). Here, in the first compensation, the frequency component of the closed resonant frequency of the sound signal is suppressed by using the compensation parameter acquired at 51602. Further, in the second compensation, the frequency component of the open resonance of the sound signal is emphasized by using the compensation parameter acquired at S1604.

Subsequently, the output module 203 outputs the sound signal on which the compensation processing is performed (S1607). As a result of the fact that the sound reproducer 110 performs the aforementioned processes, user can hear the reproduction sound without a feeling of the confined sound.

The sound reproducer 1500 of the second embodiment renders the same effect as that of the sound reproducer 110 of the first embodiment.

In the first and the second embodiment, the closed fundamental resonant frequency is suppressed, and the open fundamental resonant frequency is emphasized. However, the resonant frequencies to be compensated are not limited to the fundamental frequency. In a sound reproducer 1700 of a third embodiment, a higher order (or overtone) resonant frequency is taken into account.

Figure 17:
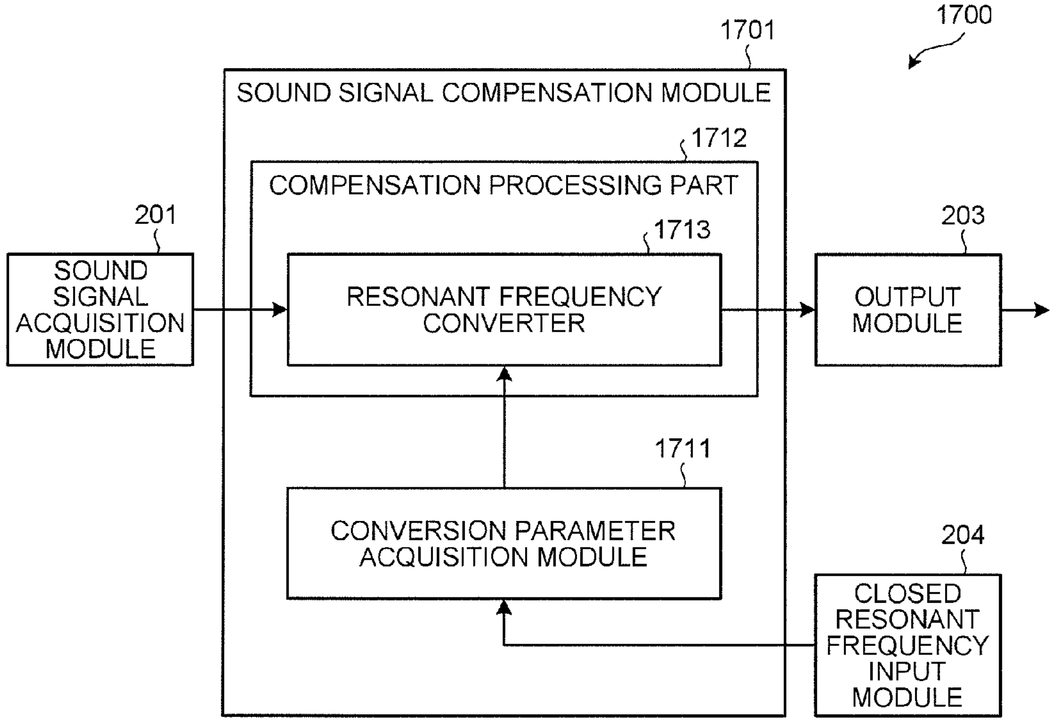
FIG. 17 is an exemplary block diagram of a sound reproducer according to a third embodiment.

FIG. 17 is an exemplary block diagram of the sound reproducer 1700 of the third embodiment. As illustrated in FIG. 17, the sound reproducer 1700 comprises the sound signal acquisition module 201, a sound signal compensation module 1701, the output module 203, and the closed resonant frequency input module 204. In the following explanations, elements similar to that of the first embodiment are labeled with the same reference numerals and/or characters, and explanations thereof are omitted.

The sound signal compensation module 1701 comprises a conversion parameter acquisition module 1711 and a compensation processing part 1712. The compensation processing part 1712 is configured by a resonant frequency converter 1713. The sound signal compensation module 1701 performs compensation processing on the sound signal.

When an earphone/headphone is removed from an ear, open ear resonances are induced. Such open ear resonances have not only the fundamental resonant frequency, but also overtone resonant frequencies. In other words, when an earphone/headphone is not worn for an ear, open ear resonances induced have resonant frequencies not only of the 1st order but also of the higher order.

Figure 18:
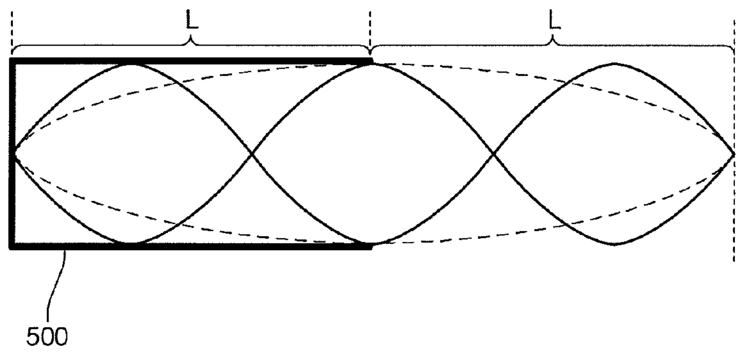
FIG. 18 is an exemplary diagram of a first model of a plurality of frequencies of open resonances induced when the earphone is removed from the ear, in the third embodiment.

FIG. 18 illustrates a plurality of open resonant frequencies in the acoustic tube 500 of the length L with a right end being opened. Note that FIG. 18 is an example that does not take into account the length δ, which is the amount of the earphone 401 squeezed into the ear canal. As illustrated in FIG. 18, in the acoustic tube 500 with one side being opened, both of the fundamental open resonance (also referred to as first order open resonance) and a third order open resonance have a node at a left end of the acoustic tube 500 and an antinode at a right end of the acoustic tube 500 which is being opened.

The sound signal compensation module 1701 performs compensation processing based on both the fundamental and the third order resonances to be induced in the acoustic tube 500 of which one side is being opened. As described above, the compensation is performed not only regarding the fundamental open resonant frequency $F_{open1}$, but also performed regarding the third order open resonant frequency $F_{open3}$. As a result, a user can be provided with a sound signal rendering no sense of discomfort.

Figure 19:
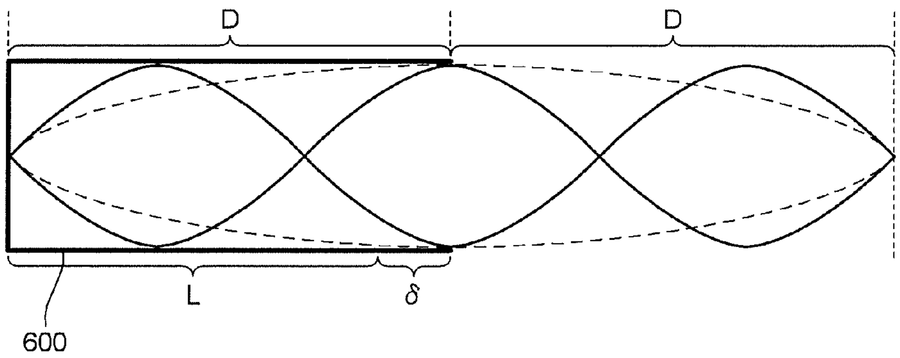
FIG. 19 is an exemplary diagram of a second model of a plurality of frequencies of open resonances induced when the earphone is removed from the ear, in the third embodiment.

The plurality of open resonances are not only induced in the model represented by FIG. 18, but also induced in other models as long as one side of the tube is opened. FIG. 19 illustrates the fundamental open resonance and the third order open resonance induced in the model represented by the acoustic tube 600 with its right end being opened and having the actual length D of the ear canal taking into account the length L of the closed space and the depth δ of when the earphone 401 is placed in the ear.

Figure 20:
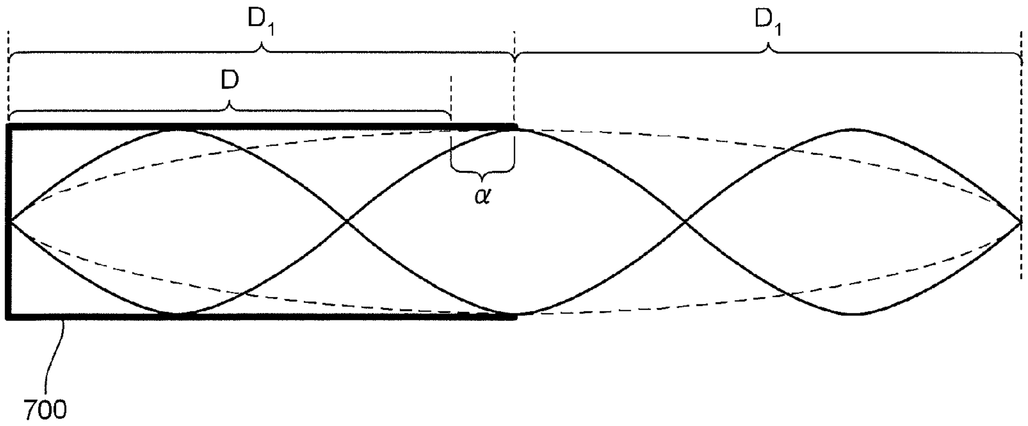
FIG. 20 is an exemplary diagram of a third model of a plurality of frequencies of open resonances induced when the earphone is removed form the ear, in the third embodiment.

FIG. 20 illustrates the fundamental open resonance and the third order open resonance induced in the model represented by the acoustic tube 700 of the length $D_1$ with its right end being opened. Here, the length $D_1$ takes into account the length L of the closed space, the depth δ of when the earphone 401 is placed in the ear, and the thickness α of the auricle.

Various techniques such as the technique of the first embodiment can be used to calculate the fundamental open resonant frequency $F_{open1}$ illustrated in FIGS. 18 to 20. Further, any techniques can be used to calculate the third order open resonant frequency $F_{open3}$ of FIGS. 18 to 20. For example, the conversion parameter acquisition module 1711 can multiply the fundamental open resonant frequency $F_{open1}$ by a predetermined number (for example, a value near 3) to obtain the third order open resonant frequency $F_{open3}$, or the third order open resonant frequency $F_{open3}$ can be obtained from the third order closed resonant frequency $F_{close3}$.

The conversion parameter acquisition module 1711 acquires a parameter for converting the fundamental closed resonant frequency to the fundamental open resonant frequency and the third order open resonant frequency, based on the identification information of the closed resonant frequency input from the closed resonant frequency input module 204. In the present embodiment, the open resonant frequency acquired by the conversion parameter acquisition module 1711 is obtained by a technique explained using FIGS. 18 to 20. For example, the fundamental closed resonant frequency $F_{close1}$ is multiplied by γ (γ is a value approximately within a range from 0.2 to 0.6) to calculate the fundamental open resonant frequency, and thereafter the fundamental closed resonant frequency is multiplied by γ' (γ' is a value near 3) to calculate the third order open resonant frequency. Actual values of γ and γ' may appropriately be set in accordance with an actual use condition such as whether to take into account the shape of the earphone and/or the thickness of the auricle.

The compensation processing part 1712 comprises the resonant frequency converter 1713, and performs compensation processing on the sound signal input from the sound signal acquisition module 201.

In the compensation control of the compensation processing part 1712, the resonant frequency converter 1713 performs the frequency conversion by using the acquired conversion parameter so that a resonant peak of the sound signal changes from the fundamental closed resonant frequency $F_{close1}$ to the fundamental open resonant frequency $F_{open1}$ and the third order open resonant frequency $F_{open3}$.

Figure 21:
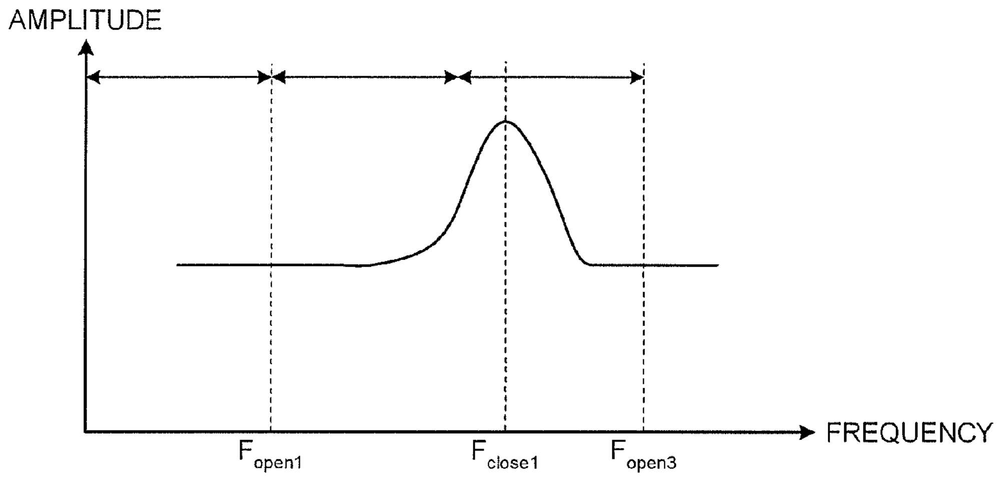
FIG. 21 is an exemplary graph of a property of a resonance phenomenon induced when an earphone/a headphone is placed in an ear and a sound source signal is output, in the third embodiment.

Next, the compensation property used in the compensation processing part 1712 is explained. FIG. 21 is a graph of a property of resonance phenomenon induced when the earphone/headphone is placed in the ear and the sound source signal is output. FIG. 21 illustrates the fundamental closed resonant frequency $F_{close1}$ specified as the resonant peak, and the fundamental open resonant frequency $F_{open1}$ and the third order open resonant frequency $F_{open3}$. The fundamental open resonant frequency $F_{open1}$ and the third order open resonant frequency $F_{open3}$ of FIG. 21 are determined from the fundamental closed resonant frequency $F_{close1}$ by the conversion parameter acquisition module 1711. That is to say, the fundamental open resonant frequency $F_{open1}$ is obtained by multiplying the fundamental closed resonant frequency $F_{close1}$ by γ (γ is a value substantially within a range from 0.2 to 0.6), and subsequently, the third order open resonant frequency $F_{open3}$ is obtained by multiplying the fundamental open resonant frequency $F_{open1}$ by γ' (γ' is a value near 3).

Figure 22:
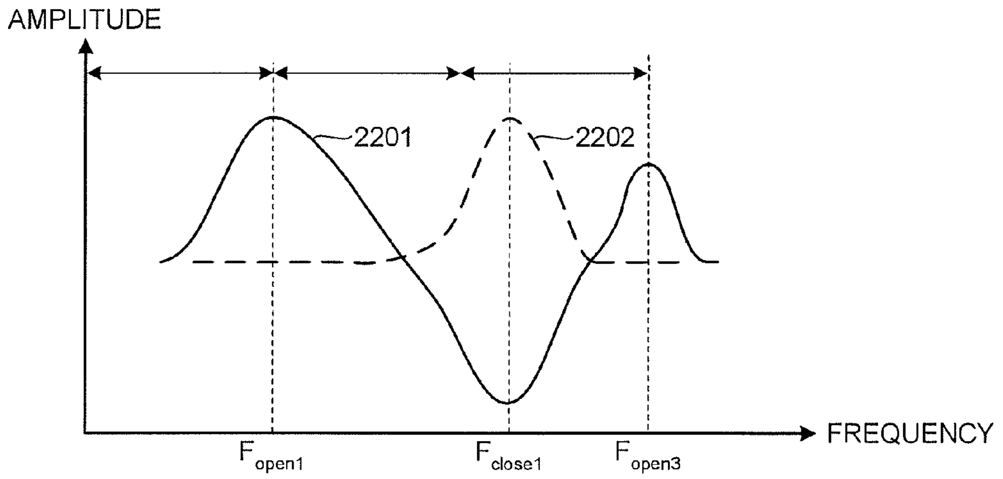
FIG. 22 is an exemplary graph of a compensation property of the compensation which is performed by the compensation processing part in the third embodiment.

Then, the compensation processing part 1712 performs the compensation by using filter coefficient information so that the fundamental open resonant frequency $F_{open1}$ and the third order open resonant frequency $F_{open3}$ each becomes the resonant peak. FIG. 22 is a graph illustrating one example of a compensation property 2201 applied by the compensation processing part 1712. The dashed line 2202 represents the property of the closed resonance phenomenon shown in FIG. 21. In the compensation property 2201 of FIG. 22, a frequency component (amplitude) of the fundamental closed resonant frequency $F_{close1}$ is suppressed and a frequency component (amplitude) of both the fundamental closed resonant frequency $F_{close1}$ and the third order open resonant frequency $F_{open3}$ higher than the fundamental closed resonant frequency $F_{close1}$ is emphasized. Here, any appropriate value may be set for each of the frequency components (amplitudes) of the fundamental closed resonant frequency $F_{close1}$, the fundamental open resonant frequency $F_{open1}$, and the third order open resonant frequency $F_{open3}$ of the compensation property 2201.

Figure 23:
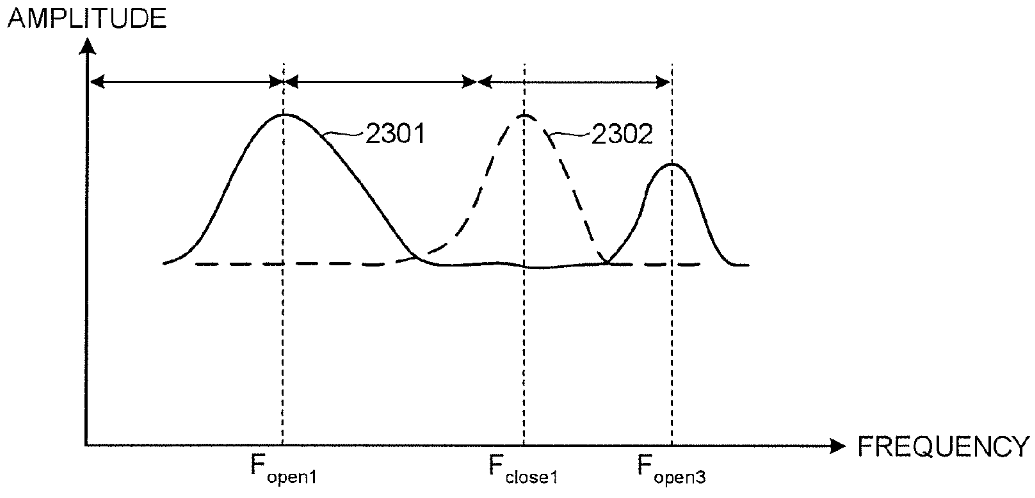
FIG. 23 is a graph of a property of compensated resonance by the compensation processing part based on the compensation property of FIG. 22 in the third embodiment.

FIG. 23 is a graph of a property 2301 of compensated resonance by the compensation property illustrated in FIG. 22 by the compensation processing part 1712. As illustrated in FIG. 23, the compensation processing part 1712 performs the compensation on a sound source signal 2202 so that the resonant peak is converted from the fundamental closed resonant frequency $F_{close1}$ to the fundamental open resonant frequency $F_{open1}$ and the third order open resonant frequency $F_{open3}$. That is to say, the resonant frequency converter 1713 of the compensation processing part 1712 compensates the sound signal by a filter C(z) with the frequency property illustrated by the solid line of FIG. 22 to realize a processing which converts the fundamental closed resonant frequency $F_{close1}$ of when the earphone/headphone is placed in the ear to the fundamental open resonant frequency $F_{open1}$ and the third order resonant frequency $F_{open3}$.

The sound reproducer 1700 of the third embodiment comprises the aforementioned configurations to take into account not only the fundamental frequency but the third order frequency as the open resonant frequencies. Accordingly, the confined sound can be reduced, and the user can be provided with open sound.

As described above, the sound reproducer 1700 of the third embodiment comprises the aforementioned configurations so as to perform the compensation by taking into account not only the fundamental resonant frequency but the third order resonant frequency as the open resonant frequency. Accordingly, in comparison to the first embodiment, the higher quality and natural open sound can be provided to the user.

In the aforementioned embodiments, the closed resonant frequency is suppressed. However, the closed resonant frequency is not necessarily required to be suppressed, and the user can be provided with an open sound only by emphasizing the open resonant frequency. Hence, as a first modification of the third embodiment, the fundamental and third order open resonant frequencies are emphasized, while the closed resonant frequency is not suppressed. The first modification is similar to the third embodiment except that the closed resonant frequency is not suppressed in the first modification. Therefore, the first modification is explained using the configurations described in the third embodiment.

Figure 24:
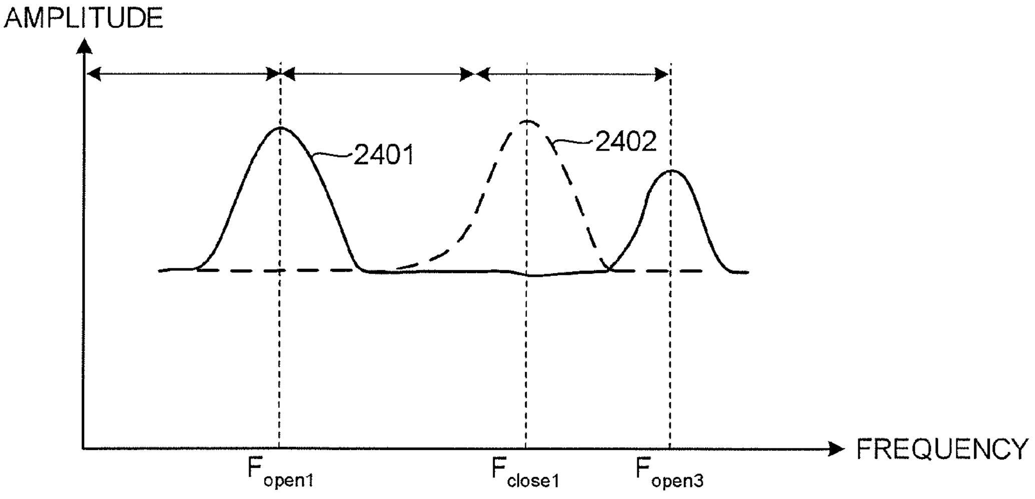
FIG. 24 is an exemplary graph of a compensation property of the compensation which is performed by the compensation processing part according to a first modification of the third embodiment.

Similar to the aforementioned embodiments, the compensation processing part 1712 of the sound reproducer 1700 of the first modification performs compensation by using filter coefficient information. FIG. 24 is a graph of a compensation property 2401 applied by the compensation processing part 1712. A dashed line 2402 represents a property of a resonance phenomenon of a sound signal in the closed space. The compensation property 2401 of FIG. 24 emphasizes frequency components (amplitudes) of the fundamental open resonant frequency $F_{open1}$ which is lower than the fundamental closed resonant frequency $F_{close1}$ and the third order open resonant frequency $F_{open3}$ which is higher than the fundamental (first order) closed resonant frequency $F_{close1}$.

Figure 25:
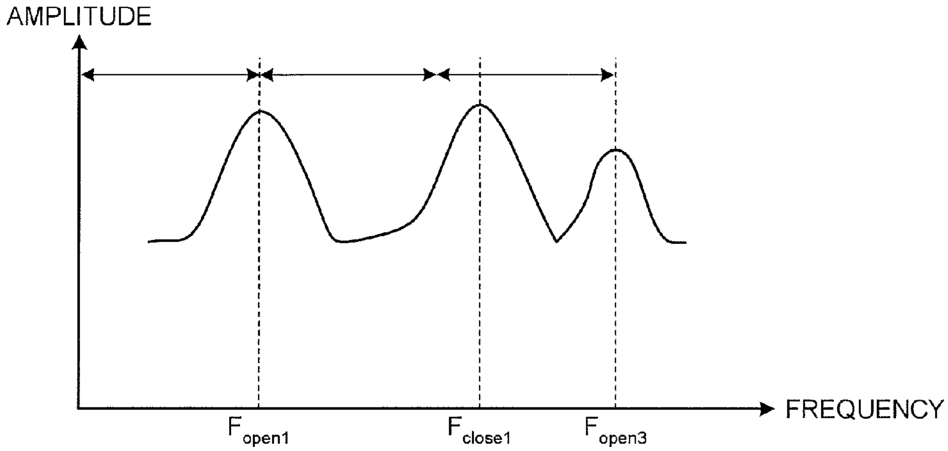
FIG. 25 is a graph of a property of compensated resonance by the compensation property of FIG. 24 by the compensation processing part in the first modification.

FIG. 25 is a graph of a property of compensated resonance by the compensation property of FIG. 24 by the compensation processing part 1712. The compensation processing part 1712 performs the compensation on the sound source signal. As a result, each of the fundamental closed resonant frequency $F_{close1}$, the fundamental open resonant frequency $F_{open1}$, and the third order open resonant frequency $F_{open3}$ becomes a resonant peak as illustrated in FIG. 25.

As described above, in the sound reproducer 1700 of the first modification of the third embodiment, the fundamental closed resonant frequency $F_{close1}$ is not suppressed while the fundamental open resonant frequency $F_{open1}$ and the third order open resonant frequency $F_{open3}$ are emphasized. Consequently, a listener can be provided with an open sound.

In the aforementioned embodiments, the fundamental closed resonant frequency is suppressed. However, the target to be suppressed is not limited to the fundamental closed resonant frequency. In a second modification of the third embodiment, not only the fundamental closed resonant frequency but a second order closed resonant frequency is also suppressed. Here, the second modification is similar to the third embodiment except that the second order closed resonant frequency is suppressed. Hence, the second modification is explained with reference to the configurations described in the third embodiment.

Figure 26:
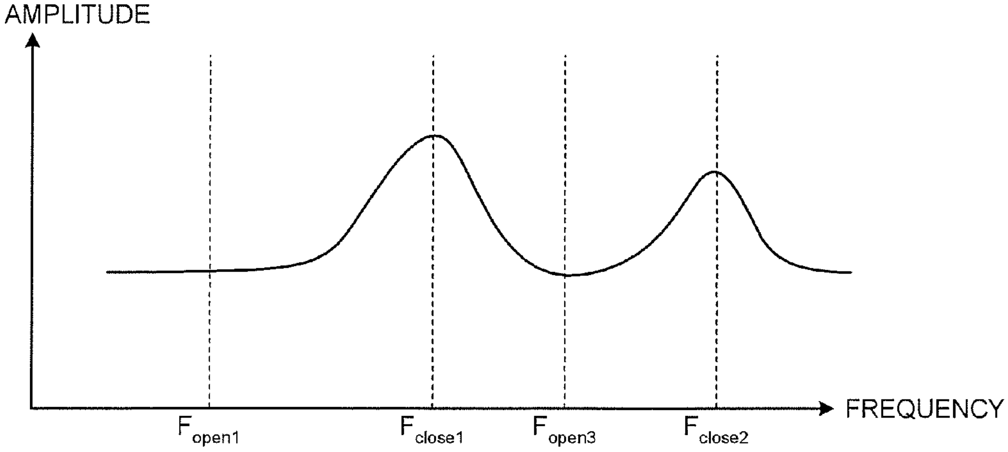
FIG. 26 is an exemplary graph of a property of a resonance phenomenon induced when an earphone/a headphone is placed in an ear and a sound source signal is output, according to a second modification of the third embodiment.

The compensation property used in the compensation processing part 1712 of the second modification of the third embodiment is explained. FIG. 26 is a graph of a property of resonance phenomenon induced when the earphone/headphone is placed in the ear and the sound source signal is output. FIG. 26 illustrates resonant peaks at the fundamental closed resonant frequency $F_{close1}$ and the second order closed resonant frequency $F_{close2}$, and illustrates the fundamental open resonant frequency $F_{open1}$ and the third order open resonant frequency $F_{open3}$. The fundamental closed resonant frequency $F_{close1}$ and the second order closed resonant frequency $F_{close2}$ illustrated in FIG. 26 can be detected by using the sound signal, or can be determined based on the user's selection. In this case, the fundamental closed resonant frequency may be selected by an operation of the user or the like, and the second order closed resonant frequency may be determined from the fundamental closed resonant frequency, based on the relation between the fundamental closed resonant frequency and the second order closed resonant frequency. The fundamental open resonant frequency $F_{open1}$ and the third order open resonant frequency $F_{open3}$ can be derived by a technique similar to that of the third embodiment.

Figure 27:
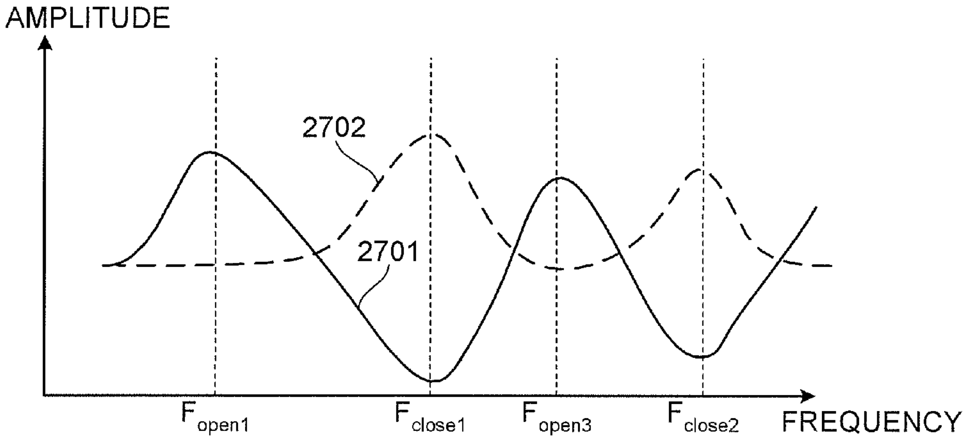
FIG. 27 is an exemplary graph of a compensation property of the compensation which is performed by the compensation processing part in the second modification.

The compensation processing part 1712 performs the compensation on the sound signal by using filter coefficient information. FIG. 27 is a graph of a compensation property 2701 applied by the compensation processing part 1712. The dashed line 2702 represents the property of the closed resonance phenomenon shown in FIG. 26. The compensation property 2701 of FIG. 27 is a graph of an example of a compensation property to suppress, the frequency components (amplitudes) of the fundamental closed resonant frequency $F_{close1}$ and the second order closed resonant frequency $F_{close2}$, and to emphasize the frequency components (amplitudes) of the fundamental open resonant frequency $F_{open1}$ and the third order open resonant frequency $F_{open3}$.

Figure 28:
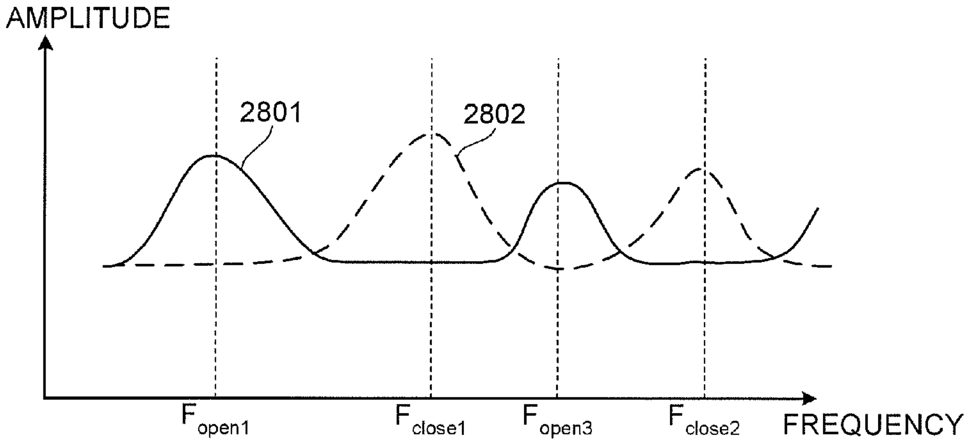
FIG. 28 is a graph of a property of compensated resonance by the compensation property of FIG. 27 by the compensation processing part in the second modification.

FIG. 28 is a graph of a property 2801 of compensated resonance by the compensation property of FIG. 27 by the compensation processing part 1712. As illustrated in FIG. 28, the compensation processing part 1712 performs compensation on the resonance property 2802 so that the resonant peaks are converted from the fundamental closed resonant frequency $F_{close1}$ and the second order closed resonant frequency $F_{close2}$ to the fundamental open resonant frequency $F_{open1}$ and the third order open resonant frequency $F_{open3}$. That is to say, the compensation processing part 1712 compensates the sound signal by a filter C(z) with the frequency property illustrated by a solid line 2701 of FIG. 27 to realize the conversion to the open resonance.

As described above, the sound reproducer 1700 of the second modification of the third embodiment performs the compensation to provide the user with higher sound quality sound than that of the third embodiment. Such high quality sound avoids unnatural sound peculiar to an earphone or a closed headphone.

A sound signal compensation program executed by the sound reproducers 110, 1500, 1700 of the aforementioned embodiments is provided by stored beforehand in a read only memory (ROM) or the like. However, the sound signal compensation program may be stored in a computer readable recording medium, such as a compact disk read only memory (CD-ROM), a flexible disk (FD), a compact disc readable (CD-R), or a digital versatile disk (DVD), as an installable or executable file, and provided.

Further, the sound signal compensation program executed by the sound reproducers 110, 1500, and 1700 of the aforementioned embodiments may be configured so as to be stored on a computer connected to a network such as the Internet, and provided by being downloaded via the network. Further, the sound signal compensation program executed by the sound reproducers 110, 1500, and 1700 of the aforementioned embodiments may be configured to be provided or distributed via the network such as the Internet.

The sound signal compensation program executed by the sound reproducers 110, 1500, and 1700 of the aforementioned embodiments comprises a module configuration comprising the aforementioned modules (sound signal acquisition module, sound signal compensation module, closed resonant frequency input module, output module). As actual hardware, the sound signal compensation program is readout from the aforementioned storage medium and executed by a central processing unit (CPU). Consequently, the each of the aforementioned modules is loaded into a main memory, and the sound signal acquisition module, the sound signal compensation module, the closed resonant frequency input module, and the output module are generated on the main memory.

The various modules of the systems described herein can be implemented as software applications, hardware and/or software modules, or components on one or more computers, such as servers. While the various modules are illustrated separately, they may share some or all of the same underlying logic or code.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A sound signal compensation apparatus comprising:

an input module configured to receive identification information identifying a first frequency with regard to a resonance of an ear closed by an earphone or headphone;

a compensation module configured to perform first compensation emphasizing a second frequency on a sound signal, the second frequency being determined based on the identification information or the first frequency as a frequency with regard to a resonance of the ear opened when the earphone or headphone is removed from the ear; and an output module configured to output the compensated sound signal, wherein the compensation module is configured to perform the first compensation emphasizing the second frequency, at which emphasis is greater than or equal to 2 dB and less than or equal to 12 dB.

2. The sound signal compensation apparatus of claim 1, wherein the compensation module is configured to further perform second compensation on the sound signal, the second compensation suppressing the first frequency.

3. The sound signal compensation apparatus of claim 2, wherein the second frequency emphasized by the compensation module is lower than the first frequency.

4. The sound signal compensation apparatus of claim 3, wherein the second frequency to be emphasized by the compensation module is less than or equal to 0.6 times the first frequency.

5. The sound signal compensation apparatus of claim 3, wherein the second frequency to be emphasized by the compensation module decreases as the first frequency decreases.

6. The sound signal compensation apparatus of claim 3, wherein the second frequency to be emphasized by the compensation module is determined based on the first frequency and a length of an ear canal in which resonance is induced when the ear is closed.

7. The sound signal compensation apparatus of claim 6, wherein the second frequency to be emphasized by the compensation module is determined based further on at least one of a depth at which the earphone or the headphone is inserted into the ear canal and a thickness of an auricle outside the ear canal.

8. The sound signal compensation apparatus of claim 1, wherein the compensation module is configured to further perform third compensation on the sound signal, the third compensation emphasizing a third frequency of which resonance order is higher than that of the second frequency.

9. A sound signal compensation method executed in a sound signal compensation apparatus, comprising:

receiving, by an input module, identification information identifying a first frequency with regard to a resonance of an ear closed by an earphone or headphone; and performing, by a compensation module, first compensation emphasizing a second frequency on a sound signal, the second frequency being determined based on the identification information or the first frequency as a frequency with regard to a resonance of the ear opened when the earphone or headphone is removed from the ear, wherein the performing performs the first compensation emphasizing the second frequency, at which emphasis is greater than or equal to 2 dB and less than or equal to 12 dB.

10. A sound signal compensation apparatus comprising:

an input module configured to receive identification information identifying a first frequency with regard to a resonance of an ear closed by an earphone or headphone;

a compensation module configured to perform first compensation emphasizing a second frequency on a sound signal, the second frequency being determined based on the identification information or the first frequency; and an output module configured to output the compensated sound signal, wherein the compensation module is configured to perform the first compensation emphasizing the second frequency, at which emphasis is greater than or equal to 2 dB and less than or equal to 12 dB as well as at which the emphasis is greater than or equal to 0.2 times the first frequency and less than or equal to 0.6 times the first frequency.

* * * * *